US00PP35619P3

(12) United States Plant Patent
Schoone

(10) Patent No.: US PP35,619 P3
(45) Date of Patent: Jan. 30, 2024

(54) ***PHALAENOPSIS* PLANT NAMED 'CHEEKY PIRATE'**

(50) Latin Name: *Phalaenopsis hybrida*
Varietal Denomination: Cheeky Pirate

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 18/130,913

(22) Filed: Apr. 5, 2023

(65) Prior Publication Data

US 2023/0329131 P1 Oct. 12, 2023

Related U.S. Application Data

(60) Provisional application No. 63/328,154, filed on Apr. 6, 2022.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02; A01H 5/00; A01H 6/82
See application file for complete search history.

(56) References Cited

U.S. PATENT DOCUMENTS

PP34,023 P3 * 3/2022 Schoone ..... A01H 6/62 Plt./311

OTHER PUBLICATIONS

CPVO Register Version 4.10.8 for *Phalaenopsis* Cheeky Pirate, retrieved on Aug. 9, 2023 at https://online.plantvarieties.eu/publicConsultationDetails?registerId=20220797&denomination=cheeky%20pirate, 2 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'Cheeky Pirate', characterized by its broadly upright plant habit; moderately vigorous growth habit; strong flowering stems; strong leaves; freely flowering habit with typically two inflorescences per plant, each inflorescence with numerous flowers; reddish purple-colored flowers with darker reddish purple-colored labellum and light pale purple-colored petal and sepal margin edges; and good postproduction longevity.

2 Drawing Sheets

Figure 1:
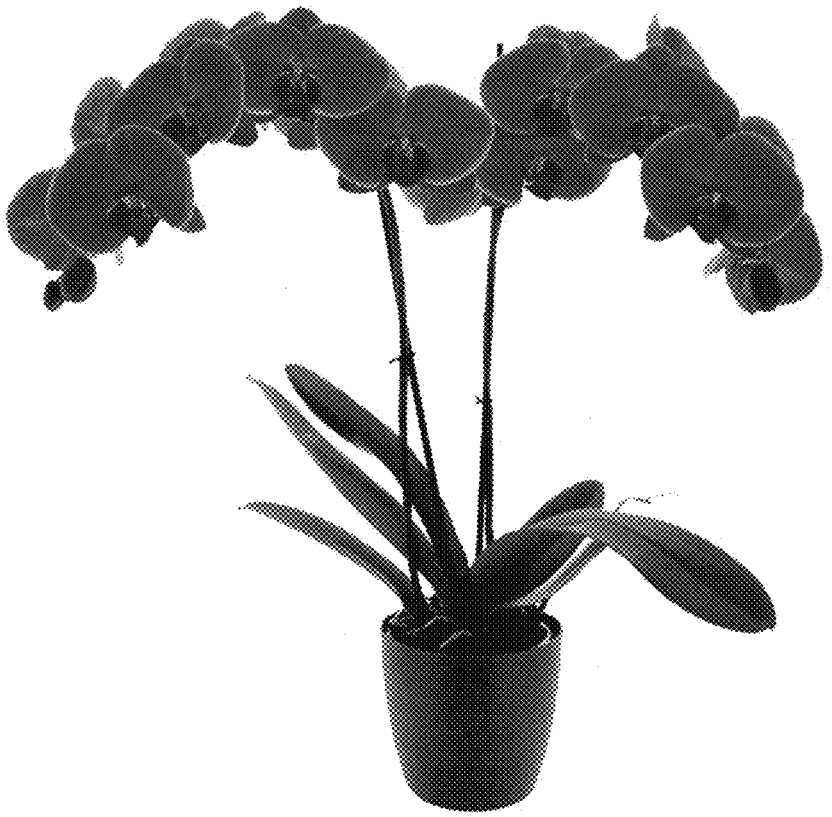

Botanical designation: *Phalaenopsis hybrida.*
Cultivar denomination: 'CHEEKY PIRATE'.

CROSS-REFERENCED TO CLOSELY-RELATED APPLICATIONS

An European Community Plant Breeder's Rights application for the instant plant was filed by the Applicant/Assignee of the instant application, Floricultura B.V. of Heemskerk, The Netherlands on Mar. 25, 2022, application number 2022/0797. Foreign priority is not claimed to this application.

BACKGROUND OF THE INVENTION

The present invention relates to a new and distinct cultivar of *Phalaenopsis* plant, botanically known as *Phalaenopsis hybrida*, and hereinafter referred to by the name 'Cheeky Pirate'.

The new *Phalaenopsis* plant is a product of a planned breeding program conducted by the Inventor in Assendelft and Heemskerk, The Netherlands. The objective of the breeding program is to develop new fast-growing and freely flowering *Phalaenopsis* plants with good leaf shape and flowers with unique and attractive patterns and coloration.

The new *Phalaenopsis* plant originated from a cross-pollination in September, 2010 in Assendelft, The Netherlands of *Phalaenopsis hybrida* 'Gypsy Queen', disclosed in U.S. Plant Pat. No. 25,509, as the female, or seed, parent with a proprietary selection of *Phalaenopsis hybrida* identified as code number 50M0323, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in June, 2018.

Asexual reproduction of the new *Phalaenopsis* plant by in vitro meristem propagation in a controlled environment in Assendelft, The Netherlands since June, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Cheeky Pirate'. These characteristics in combination distinguish 'Cheeky Pirate' as a new and distinct *Phalaenopsis* plant:

1. Broadly upright plant habit.
2. Moderately vigorous growth habit.
3. Strong flowering sterns.
4. Strong leaves.
5. Freely flowering habit with typically two inflorescences per plant, each inflorescence with numerous flowers.
6. Reddish purple-colored flowers with darker reddish purple-colored labellum and light pale purple-colored petal and sepal margin edges.
7. Good postproduction longevity.

Plants of the new *Phalaenopsis* can be compared to plants of the female parent, 'Gypsy Queen'. Plants of the new *Phalaenopsis* differ primarily from plants of 'Gypsy Queen' in flower color as flowers of plants of the new *Phalaenopsis* have much less netting and stripes compared to flowers of plants of 'Gypsy Queen'.

Plants of the new *Phalaenopsis* can be compared to plants of the male parent selection. Plants of the new *Phalaenopsis* differ primarily from plants of the male parent selection in flower color as flowers of plants of the new *Phalaenopsis* have a small amount of netting and stripes whereas flowers of plants of the male parent selection do not have any netting or stripes.

Plants of the new *Phalaenopsis* can be compared to plants of *Phalaenopsis hybrida* 'Time Bandit', disclosed in U.S. Provisional Patent application Ser. No. 63/430,035. In side-by-side comparisons, plants of the new *Phalaenopsis* differ primarily from plants of 'Time Bandit' in flower color as flowers of plants of the new *Phalaenopsis* have a small amount of netting and stripes whereas flowers of plants of 'Time Bandit' do not have any netting or stripes. In addition, petals of plants of the new *Phalaenopsis* are "touching" (imbricate) whereas petals of plants of 'Time Bandit' are "free" (not imbricate).

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Cheeky Pirate' grown in a container.

Figure 2:
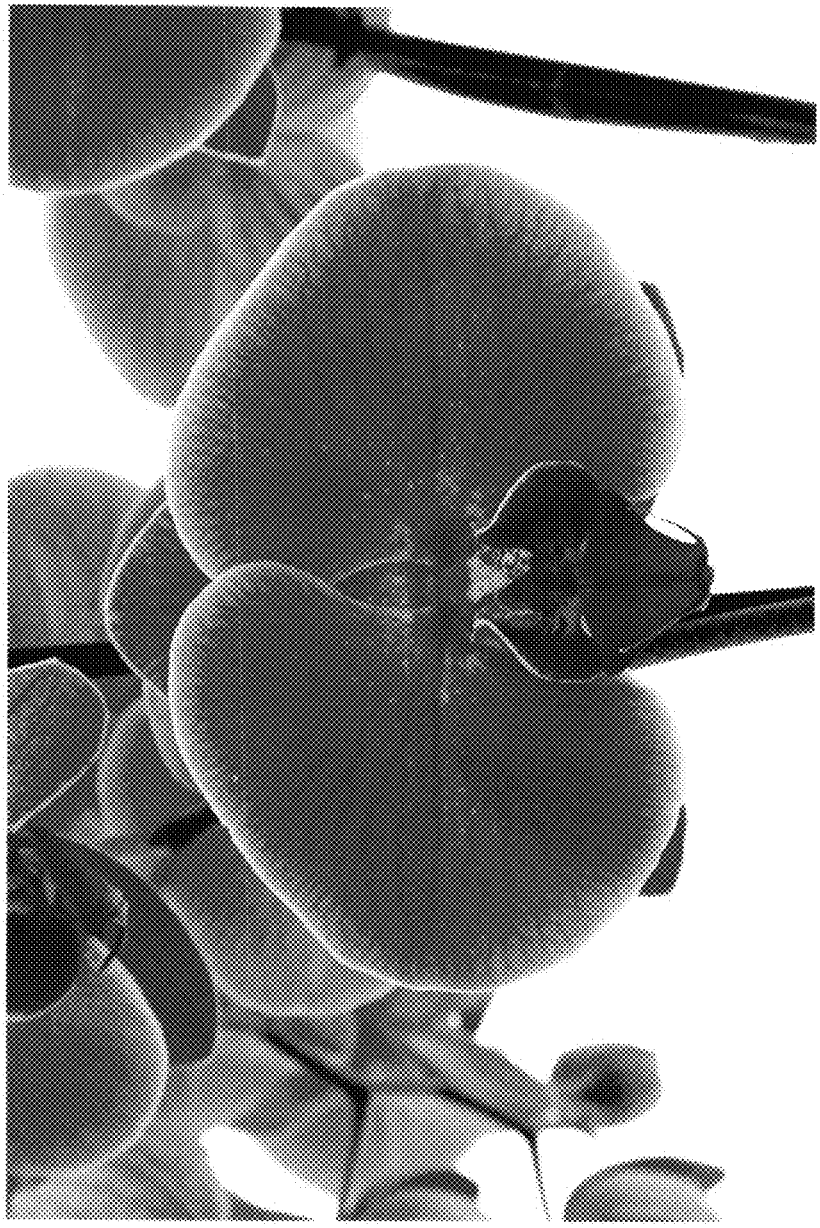

The photograph on the second sheet (FIG. 2) is a close-up view of typical flowers of 'Cheeky Pirate'.

DETAILED BOTANICAL DESCRIPTION

The aforementioned photographs and following observations and measurements describe plants grown during the late summer in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27 C. During the final six months of production of the plants, day temperatures ranged from 20 C to 22 C and night temperatures ranged from 18 C to 20 C. During the production of the plants, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Cheeky Pirate'.

Parentage:

*Female, or seed, parent.*—*Phalaenopsis hybrida* 'Gypsy Queen', disclosed in U.S. Plant Pat. No. 25,509.

*Male parent.*—Proprietary breeding selection of *Phalaenopsis hybrida* identified as code number 50M0323, not patented.

Propagation:

*Type.*—By in vitro meristem propagation.

*Time to initiate roots, summer and winter.*—About two weeks at temperatures about 28 C to 30 C.

*Time to produce a rooted young plant, summer and winter.*—About 20 to 25 weeks at temperatures about 28 C to 30 C.

*Root description.*—Thin, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; broadly upright plant habit with typically two inflorescences per plant, each inflorescence with numerous flowers; monopodial; moderately vigorous growth habit and moderate growth rate.

*Plant height, substrate level to top of foliar plane.*—About 19.8 cm.

*Plant height, substrate level to top of inflorescences.*—About 41.9 cm.

*Plant diameter or spread.*—About 27.3 cm.

Leaf description:

*Arrangement and quantity.*—Distichous, simple; sessile; about five leaves per plant.

*Length.*—About 20.6 cm.

*Width.*—About 7 cm.

*Aspect.*—Upright to outwardly arching.

*Shape.*—Narrowly obovate to oblanceolate; slightly carinate.

*Apex.*—Unequal obtuse to unequal and broadly acute.

*Base.*—Sheathing. Sheath length: About 1.9 cm. Sheath width: About 1.4 cm. Sheath color: Close to 143C; towards the margins, tinged with close to 176B.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to NN137A. Developing leaves, lower surface: Close to 146A; towards the margins and along the midvein, tinged with close to N186C. Fully expanded leaves, upper surface: Close to NN137B; venation, close to 147A. Fully expanded leaves, lower surface: Close to 146A to 146B; towards the margins, tinged with close to N186C; venation, close to 144A.

Inflorescence description:

*Appearance and flowering habit*.—Showy zygomorphic flowers arranged on axillary branched racemes; typically two inflorescences per plant; each inflorescence with about nine flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about six months after planting; plants flower naturally during the winter into the spring.

*Flower longevity*.—Long flowering period, individual flowers maintain good substance for about ten weeks on the plant; flowers not persistent.

*Inflorescence length* (*lowermost flower to inflorescence apex*).—About 29.4 cm.

*Inflorescence width*.—About 14.8 cm.

*Flower buds*.—Height: About 2.2 cm. Diameter: About 1.7 cm by 1.9 cm. Shape: Broadly ovate. Color: Slightly darker than N77A; towards the base, tinged with close to 177C to 177D.

*Flower size*.—About 7.6 cm (vertical) by 9.7 cm (horizontal).

*Flower depth*.—About 3.2 cm.

*Lateral petals*.—Quantity and arrangement: Three, two lateral petals and one center petal transformed into a labellum. Length: About 4.6 cm. Width: About 6.2 cm. Shape: Roughly reniform. Apex: Obtuse to broadly and shallowly retuse. Margin: Entire. Texture and luster, upper and lower surfaces: Smooth, glabrous, velvety; matte. Color: When opening, upper surface: Slightly darker than N78A; towards the base, close to N78A to a blend of N78A to N78B; at the base, slightly darker than N78A; sparse and fine central dots, close to 76C. When opening, lower surface: Close to N78B to slightly darker towards the margins; towards the base, close to N75A; venation, close to N78A and N78B. Fully opened, upper surface: Close to a blend of N78A and NN78A; towards the base, close to N78B; at the base, close to NN78A; narrow margin edges, close to 76C; sparse to moderate and fine central dots, close to 76C; venation, close to N78A; color does not change with subsequent development. Fully opened, lower surface: Close to N78C; towards the base, close to N80B to N80C; narrow margin edges, close to 76C; venation, close to N78B; color does not change with subsequent development.

*Labella*.—Appearance: Three-parted with two lateral lobes and a central lobe. Length, lateral lobes: About 2.3 cm. Width, lateral lobes: About 1.6 cm. Length, central lobe: About 2.4 cm. Width, central lobe: About 8 mm to 20 mm. Length, cirrose tips: About 1.2 cm. Shape, lateral lobes: Obovate. Shape, central lobe: Deltoid with a slightly elongated apex. Apex, lateral lobes: Obtuse. Apex, central lobe: Cleft with two recurved cirrose apices. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 6 mm in length, about 7 mm in width and about 3 mm in height. Color: When opening, upper surface: Lateral lobes: Close to N79C; upper margin edges, close to 157A; towards the base, stripes, close to N155A. Central lobe: Close to a blend of NN78A and N79C; towards the base, close to N79C; at the base, close to 75B and 75C; radial stripes, close to N79C; cirrose apices, close to N79C. Callosities: Close to 12B to 12C with fine dots, close to 187C. When opening, lower surface: Lateral lobes: Upper half, close to N79C and lower half, close to 156C. Central lobe: Close to NN78A; towards the margins, apex and cirrose apices, close to N79C; center, close to 76A; at the base, close to N155A. Fully opened, upper surface: Lateral lobes: Close to N78A; towards the base, close to N79C; upper margin edges, close to 79D; towards the base, stripes, close to N155A slightly tinged with close to 12B. Central lobe: Close to NN78A; at the wide parts of the base, close to 164A; at the base, close to 75B and 75C; radial stripes, close to N79C; cirrose apices, close to a blend of NN78A and N79C. Callosities: Close to 12B and 21A with fine dots, close to 187C. Fully opened, lower surface: Lateral lobes: Center, close to N78A; above the center, close to N79C and below the center, close to 156C. Central lobe: Close to NN78A; towards the margins, apex and cirrose apices, close to N79C; center, close to 76A; at the wide parts of the base, close to 164C and at the base, close to N155A.

*Sepals*.—Quantity and arrangement: Three, one upper dorsal sepal and two lower lateral sepals. Length, dorsal and lateral sepals: About 4.6 cm. Width, dorsal sepal: About 3.7 cm. Width, lateral sepal: About 3.1 cm. Shape, dorsal sepal: Broadly elliptic. Shape, lateral sepals: Ovate. Apex, dorsal sepal: Obtuse to broadly and bluntly acute. Apex, lateral sepals: Broadly and bluntly acute. Base, dorsal and lateral sepals: Truncate. Margin, dorsal and lateral sepals: Entire. Texture and luster, dorsal and lateral sepals, upper and lateral surfaces: Smooth, glabrous, moderately velvety; matte. Color, dorsal sepal: When opening, upper surface: Close to N78A to slightly darker than N78A; venation, close to N79C; moderate and fine dots, close to 76C. When opening, lower surface: Close to a blend of N77B and 186B; venation, close to N79D; moderate and fine dots, close to 76C. Fully opened, upper surface: Close to N78A; towards the margins, close to N78B to N78C; marginal edges, close to 76C; at the base, close to a blend of N78A and N79C; venation, slightly darker than N78A; moderate and fine dots, close to 76C. Fully opened, lower surface: Close to N78C; towards the base, close to N78D; venation, close to N78A to N78B; moderate and fine dots, close to 76C. Color, lateral sepals: When opening, upper surface: Close to a blend of N78A and N79C; center, close to N78B; at the base, close to 145D; venation, close to N79C; dense and fine dots, close to 76D. When opening, lower surface: Close to a blend of 182D and 196B; venation, close to N77B. Fully opened, upper surface: Close to N78A; center, close to N78B; at the base, close to 145D; narrow margin edge, close to 76C; venation, close to a blend of N78A and N79C; dense and fine dots, close to 76D. Fully opened, lower surface: Close to N78D; at the base, tinged with close to 145C; venation, close to NN78A; moderate and fine dots, close to 76C.

*Peduncles*.—Length: About 54.9 cm. Diameter: About 5.5 mm. Strength: Strong. Aspect: Upright to outwardly arching. Texture and luster: Smooth, glabrous; matte. Color: Close to a blend of 197A and N200A; densely covered with fine dots and marbling, close to 148B.

*Pedicels*.—Length: About 3.5 cm. Diameter: About 3 mm. Strength: Moderately strong. Aspect: About 70 degrees from peduncle axis. Texture and luster: Smooth, glabrous; matte. Color: Close to N148D; proximally, strongly tinged with close to 177B; distally, close to 157D and slightly tinged with close to 75C.

*Reproductive organs*.—Androecium: Column length: About 9 mm. Column width: About 6 mm. Column color: Close to N78A and N78B. Pollinia quantity: Two. Pollinia diameter (per two pollinia): About 2 mm. Pollinia color: Close to 25A. Gynoecium: Stigma length: About 3.5 mm. Stigma width: About 5 mm. Stigma shape: Reniform. Stigma color: Close to N155A. Ovary length: About 6 mm. Ovary diameter: About 1 mm. Ovary color: Close to 150C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40 C and are suitable for USDA Hardiness Zones 10 to 12.

It is claimed:

1. A new and distinct *Phalaenopsis* plant named 'Cheeky Pirate' as illustrated and described.

* * * * *